(12) United States Patent
Drake et al.

(10) Patent No.: US 6,239,331 B1
(45) Date of Patent: May 29, 2001

(54) ENHANCEMENT OF TOMATO PHYTOENE SYNTHASE GENE EXPRESSION WITH A MODIFIED DNA

(75) Inventors: Caroline Rachel Drake; Colin Roger Bird, both of Bracknell; Wolfgang Walter Schuch, Crowthorne, all of (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/180,342

(22) PCT Filed: May 23, 1997

(86) PCT No.: PCT/GB97/01414
§ 371 Date: Nov. 5, 1998
§ 102(e) Date: Nov. 5, 1998

(87) PCT Pub. No.: WO97/46690
PCT Pub. Date: Dec. 11, 1997

(30) Foreign Application Priority Data

Jun. 7, 1996 (GB) .................................................. 9611981

(51) Int. Cl.[7] .................................................. C12N 15/82
(52) U.S. Cl. ........................................ 800/282; 435/320.1
(58) Field of Search ............................... 435/69.1, 320.1, 435/419, 468, 440; 536/23.2, 23.6; 800/278, 282, 298, 317.4

(56) References Cited

FOREIGN PATENT DOCUMENTS

WO96/02650 * 2/1998 (WO) .

OTHER PUBLICATIONS

Stam M, et al. "The silence of genes in transgenic plants." Ann. Bot. 79: 3–12, 1997.*
Koziel MG, et al. "Optimizing expression of transgenes with an emphasis on post–transcriptional events." Plant Mol. Biol. 32: 393–405, 1996.*
Smith CJS, et al. "Antisense RNA inhibition of polygalacturonase gene expression in transgenic tomatoes." Nature 334: 724–726, Aug. 25, 1988.*

* cited by examiner

*Primary Examiner*—Amy J. Nelson
(74) *Attorney, Agent, or Firm*—Liza D. Hohenschutz

(57) ABSTRACT

A method for enhancing the expression of a tomato phytoene synthese gene in a plant while avoiding or reducing co-suppression involves the synthesis of a DNA which is altered in nucleotide sequence (SEQ ID NO:1) and is capable of expression of a protein, ideally identical to that of a protein already expressed by a DNA already present in the plant. This method ensures that sequence similarity between the two genes is reduced enough to eliminate the phenomenon of co-suppression, allowing the over-expression of a specific phytoene synthese protein.

5 Claims, 2 Drawing Sheets

SEQUENCE LISTING

<160> NUMBER OF SEQ ID NOS: 3

<210> SEQ ID NO 1
<211> LENGTH: 1239
<212> TYPE: DNA
<213> ORGANISM: Artificial Sequence
<220> FEATURE:
<223> OTHER INFORMATION: Description of Artificial Sequence:Synthetic DNA

<400> SEQUENCE: 1

```
atgagcgtgg cacttctttg ggtggtgagc ccatgcgatg tgagtaacgg cacttcattt    60
atggagagtg tgagagaagg taatagattc ttcgacagtt ctcgtcaccg taaccttgtt   120
agtaacgaac gtataaacag gggaggaggt aaacagacaa caacggtag aaagttctca    180
gttagatcag caatccttgc aacacctagc ggtgagagaa ctatgactag cgagcaaatg   240
gtgtacgacg tcgtacttcg tcaagctgca ctagttaaac gtcagttacg tagtactaac   300
gaacttgagg ttaaacctga cattccaata cctggaaacc ttggacttct ttctgaggct   360
tacgacagat gcggagaggt ttgcgcagaa tacgctaaaa ccttcaattt gggtaccatg   420
ttgatgacac cagaaaggcg tcgtgcaata tgggctattt acgtttggtg taggcgtact   480
gacgagttag tggacggacc taatgctagt tacataacac ccgctgctct tgacagatgg   540
gagaaccgtt tggaggacgt gtttaacggc agacctttcg atatgttgga cggagcactt   600
agtgacactg tgagcaattt ccctgtggac atccaacctt tcgggacat  gatcgagggc    660
atgagaatgg atcttcgtaa gtctcgttat aagaattttg atgagttgta tttgtactgc   720
tactacgtgg caggaaccgt gggccttatg tcagtgccta tcatgggaat tgcaccagag   780
agtaaagcta ctactgaatc tgtttacacc gcagcactag cattaggtat agctaaccag   840
cttacaaata tcttgaggga cgtgggtgag gacgcacgta ggggtcgtgt gtatctccca   900
caggacgagc tcgctcaagc tggattgagt gacgaggaca ttttcgcagg tcgtgttaca   960
gacaagtgga ggatttttcat gaaaaagcag attcaccgtg ctcgtaaatt tttcgacgaa  1020
gctgaaaagg gagttactga gctttctagt gcatcaaggt ttccagtttg ggccagcctt  1080
gtgctctata gaaagatttt ggacgaaatc gaggctaacg attataataa ttttactaaa  1140
cgtgcttacg tttctaagag caaaaaactt atcgctcttc caatcgctta cgctaagagc  1200
```

-continued

```
ttggttccac caactaagac agctagcttg cagaggtga                              1239

<210> SEQ ID NO 2
<211> LENGTH: 1239
<212> TYPE: DNA
<213> ORGANISM: Lycopersicon esculentum

<400> SEQUENCE: 2
atgtctgttg ccttgttatg ggttgtttct ccttgtgacg tctcaaatgg gacaagtttc     60
atggaatcag tccgggaggg aaaccgtttt tttgattcat cgaggcatag gaatttggtg    120
tccaatgaga gaatcaatag aggtggtgga aagcaaacta ataatggacg gaaattttct    180
gtacggtctg ctattttggc tactccatct ggagaacgga cgatgacatc ggaacagatg    240
gtctatgatg tggttttgag gcaggcagcc ttggtgaaga ggcaactgag atctaccaat    300
gagttagaag tgaagccgga tatacctatt ccggggaatt tgggcttgtt gagtgaagca    360
tatgataggt gtggtgaagt atgtgcagag tatgcaaaga cgtttaactt aggaactatg    420
ctaatgactc ccgagagaag aagggctatc tgggcaatat atgtatggtg cagaagaaca    480
gatgaacttg ttgatggccc aaacgcatca tatattaccc cggcagcctt agataggtgg    540
gaaaataggc tagaagatgt tttcaatggg cggccatttg acatgctcga tggtgctttg    600
tccgatacag tttctaactt ccagttgat attcagccat tcagagatat gattgaagga    660
atgcgtatgg acttgagaaa atcgagatac aaaaacttcg acgaactata cctttattgt    720
tattatgttg ctggtacggt tgggttgatg agtgttccaa ttatgggtat cgcccctgaa    780
tcaaaggcaa caacagagag cgtatataat gctgctttgg ctctggggat cgcaaatcaa    840
ttaactaaca tactcagaga tgttggagaa gatgccagaa gaggaagagt ctacttgcct    900
caagatgaat tagcacaggc aggtctatcc gatgaagata tatttgctgg aagggtgacc    960
gataaatgga gaatctttat gaagaaacaa atacataggg caagaaagtt ctttgatgag   1020
gcagagaaag gcgtgacaga attgagctca gctagtagat ccctgtatg ggcatctttg    1080
gtcttgtacc gcaaaatact agatgagatt gaagccaatg actacaacaa cttcacaaag   1140
agagcatatg tgagcaaatc aaagaagttg attgcattac ctattgcata tgcaaaatct   1200
cttgtgcctc ctacaaaaac tgcctctctt caaagataa                          1239

<210> SEQ ID NO 3
<211> LENGTH: 402
<212> TYPE: PRT
<213> ORGANISM: Lycopersicon esculentum

<400> SEQUENCE: 3

Met Ser Val Ala Leu Leu Trp Val Val Ser Pro Cys Asp Val Ser Asn
  1               5                  10                  15

Gly Thr Ser Phe Met Glu Ser Val Arg Glu Gly Asn Arg Phe Phe Asp
                 20                  25                  30

Ser Ser Arg His Arg Asn Leu Val Ser Asn Glu Arg Ile Asn Arg Gly
             35                  40                  45

Gly Gly Lys Gln Thr Asn Asn Gly Arg Lys Phe Ser Val Arg Ser Ala
         50                  55                  60

Ile Leu Ala Thr Pro Ser Gly Glu Arg Thr Met Thr Ser Glu Gln Met
 65                  70                  75                  80

Val Tyr Asp Val Val Leu Arg Gln Ala Ala Leu Val Lys Arg Gln Leu
                 85                  90                  95

Arg Ser Thr Asn Glu Leu Glu Val Lys Pro Asp Ile Pro Ile Pro Gly
```

-continued

```
                         100                 105                 110
Asn Leu Gly Leu Leu Ser Glu Ala Tyr Asp Arg Cys Gly Glu Val Cys
            115                 120                 125
Ala Glu Tyr Ala Lys Thr Phe Asn Leu Gly Thr Met Leu Met Thr Pro
    130                 135                 140
Glu Arg Arg Ala Ile Trp Ala Ile Tyr Val Trp Cys Arg Arg Thr
145                 150                 155                 160
Asp Glu Leu Val Asp Gly Pro Asn Ala Ser Tyr Ile Thr Pro Ala Ala
                165                 170                 175
Leu Asp Arg Trp Glu Asn Arg Leu Glu Asp Val Phe Asn Gly Arg Pro
                180                 185                 190
Phe Asp Met Leu Asp Gly Ala Leu Ser Asp Thr Val Ser Asn Phe Pro
                195                 200                 205
Val Asp Ile Gln Pro Phe Arg Asp Met Ile Glu Gly Met Arg Met Asp
    210                 215                 220
Leu Arg Lys Ser Arg Tyr Lys Asn Phe Asp Glu Leu Tyr Leu Tyr Cys
225                 230                 235                 240
Tyr Tyr Val Ala Gly Thr Val Gly Leu Met Ser Val Pro Ile Met Gly
                245                 250                 255
Ile Ala Pro Glu Ser Lys Ala Thr Thr Glu Ser Val Tyr Asn Ala Ala
                260                 265                 270
Leu Ala Leu Gly Ile Ala Asn Gln Leu Thr Asn Ile Leu Arg Asp Val
                275                 280                 285
Gly Glu Asp Ala Arg Arg Gly Arg Val Tyr Leu Pro Gln Asp Glu Leu
    290                 295                 300
Ala Gln Ala Gly Leu Ser Asp Glu Asp Ile Phe Ala Gly Arg Val Thr
305                 310                 315                 320
Ile His Arg Ala Arg Lys Phe Phe Asp Glu Ala Glu Lys Gly Val Thr
                325                 330                 335
Glu Leu Ser Ser Ala Ser Arg Phe Pro Val Trp Ala Ser Leu Val Leu
                340                 345                 350
Tyr Arg Lys Ile Leu Asp Glu Ile Glu Ala Asn Asp Tyr Asn Asn Phe
                355                 360                 365
Thr Lys Arg Ala Tyr Val Ser Lys Ser Lys Leu Ile Ala Leu Pro
    370                 375                 380
Ile Ala Tyr Ala Lys Ser Leu Val Pro Pro Thr Lys Thr Ala Ser Leu
385                 390                 395                 400
Gln Arg
```

ENHANCEMENT OF TOMATO PHYTOENE SYNTHASE GENE EXPRESSION WITH A MODIFIED DNA

BACKGROUND OF THE INVENTION

This invention relates to a method and material for enhancing gene expression in organisms, particularly in plants. One particular, but not exclusive, application of the invention is the enhancement of caroteniod biosynthesis in plants such as tomato (Lycopersicon spp.)

In order to increase production of a protein by an organism, it is known practice to insert into the genome of the target organism one or more additional copies of the protein-encoding gene by genetic transformation. Such copies would normally be identical to a gene which is already present in the plant or, alternatively, they may be identical copies of a foreign gene. In theory, multiple gene copies should, on expression cause the organism to produce the selected protein in greater than normal amounts, this is referred to as "overexpression". Experiments have shown however, that low expression or no expression of certain genes can result when multiple copies of the gene are present. (Napoli et al 1990 and Dorlhac de Borne et al 1994). This phenomenon is referred to as co-suppression. It most frequently occurs when recombinant genes are introduced into a plant already containing a gene similar in nucleotide sequence. It has also been observed in endogenous plant genes and transposable elements. The effects of co-suppression are not always immediate and can be influenced by developmental and environmental factors in the primary transformants or in subsequent generations.

The general rule is to transform plants with a DNA sequence the codon usage of which approximates to the codon frequency used by the plant. Experimental analysis has shown that introducing a second copy of a gene identical in sequence to a gene already in the plant genome can result (in some instances) with the expression of the transgene, endogenous gene or both genes being inactivated (co-suppression). The mechanisms of exactly how co-suppression occurs are unclear, however there are several theories incorporating both pre- and post-gene transcriptional blocks.

As a rule the nucleotide sequence of an inserted gene is "optimised" in two respects. The codon usage of the inserted gene is modified to approximate to the preferred codon usage of the species into which the gene is to be inserted. Inserted genes may also be optimised in respect of the nucleotide usage with the aim of approximating the purine to pyrimidine ratio to that commonly found in the target species. When genes of bacterial origin are transferred to plants, for example, it is well known that the nucleotide usage has to be altered to avoid highly adenylated regions, common in bacterial genes, which may be misread by the eukaryotic expression machinery as a polyadenylation signal specifying termination of translation, resulting in truncation of the polypeptide. This is all common practice and is entirely logical that an inserted sequence should mimic the codon and nucleotide usage of the target organism for optimum expression.

An object of the present invention is to provide means by which co-suppression may be obviated or mitigated.

SUMMARY OF THE INVENTION

According to the present invention there is provided a method of enhancing expression of a selected protein by an organism having a gene which produces said protein, comprising inserting into a genome of the said organism a DNA the nucleotide sequence of which is such that the RNA produced on transcription is different from but the protein produced on translation is the same as that expressed by the gene already present in the genome.

The invention also provides a gene construct comprising in sequence a promoter which is operable in a target organism, a coding region encoding a protein and a termination signal characterised in that the nucleotide sequence of the said construct is such that the RNA produced on transcription is different from but the protein produced on translation is the same as that expressed by the gene already present in the genome.

The inserted sequence may have a constitutive promoter or a tissue or developmental preferential promoter.

It is preferred that the promoter used in the inserted construct be different from that used by the gene already present in the target genome. However, our evidence suggests that it may be sufficient that the region between the transcription and translation initiation codons, sometimes referred to as the "5' intervening region", be different. In other words, the co-suppression phenomenon is probably associated with the transcription step of expression rather than the translation step: it occurs at the DNA or RNA levels or both.

The invention further provides transgenic plants having enhanced ability to express a selected gene and seed and propagating material derived from the said plant.

This invention is of general applicability to the expression of genes but will be illustrated in one specific embodiment of our invention by a method of enhancing expression of the phytoene synthase gene which is necessary for the biosynthesis of carotenoids in plants, the said overexpression being achieved by the use of a modified transgene having a different nucleotide sequence from the endogenous sequence.

Preferably said modified phytoene synthase gene has the sequence SEQ-ID-NO-1.

The invention also provides a modified chloroplast targeting sequence comprising nucleotides 1 to 417 of SEQ-ID-NO-1.

DETAILED DESCRIPTION OF THE INVENTION

Figure 1:
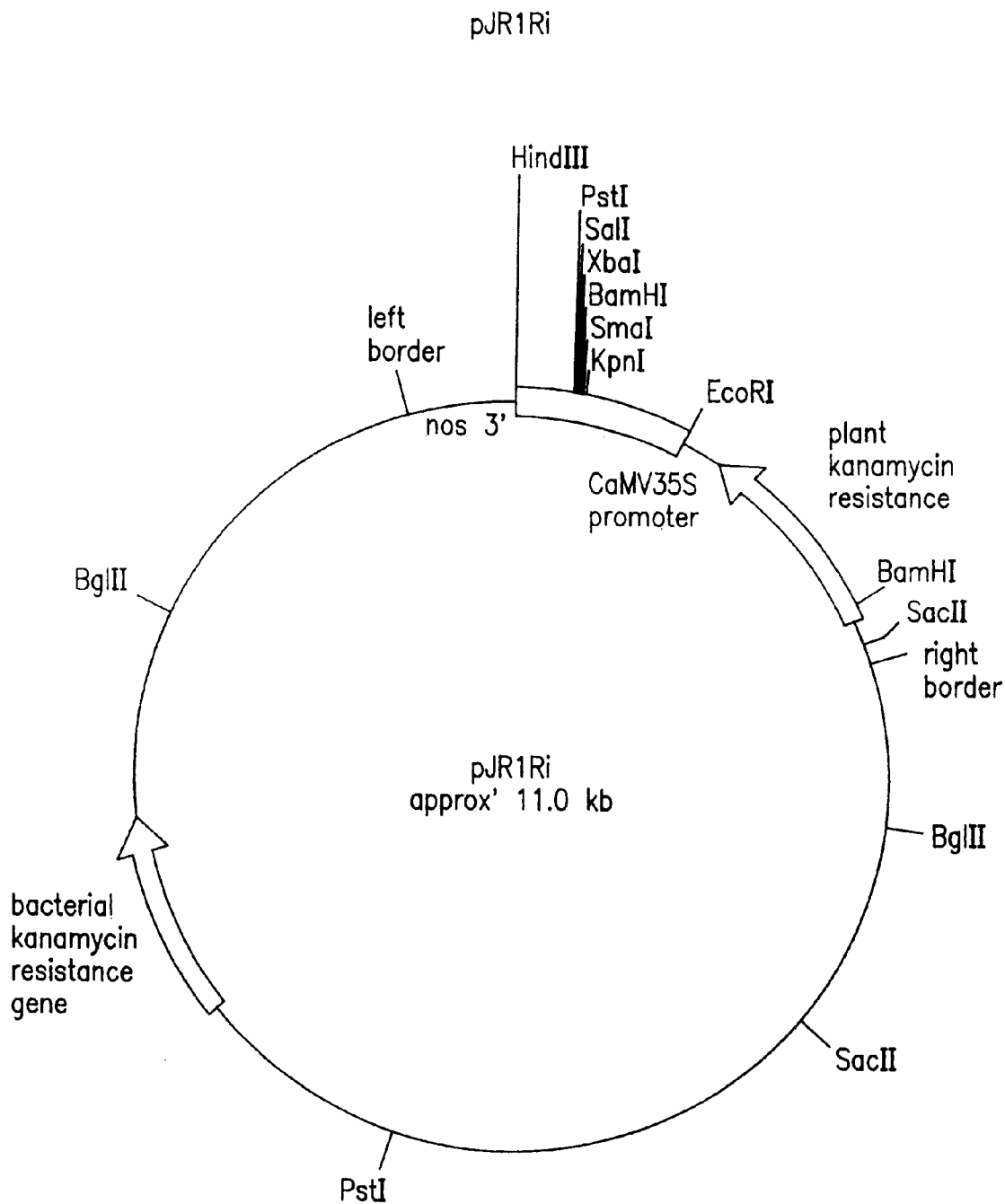
FIG. 1 shows the vector pJR1Ri.
Figure 2:
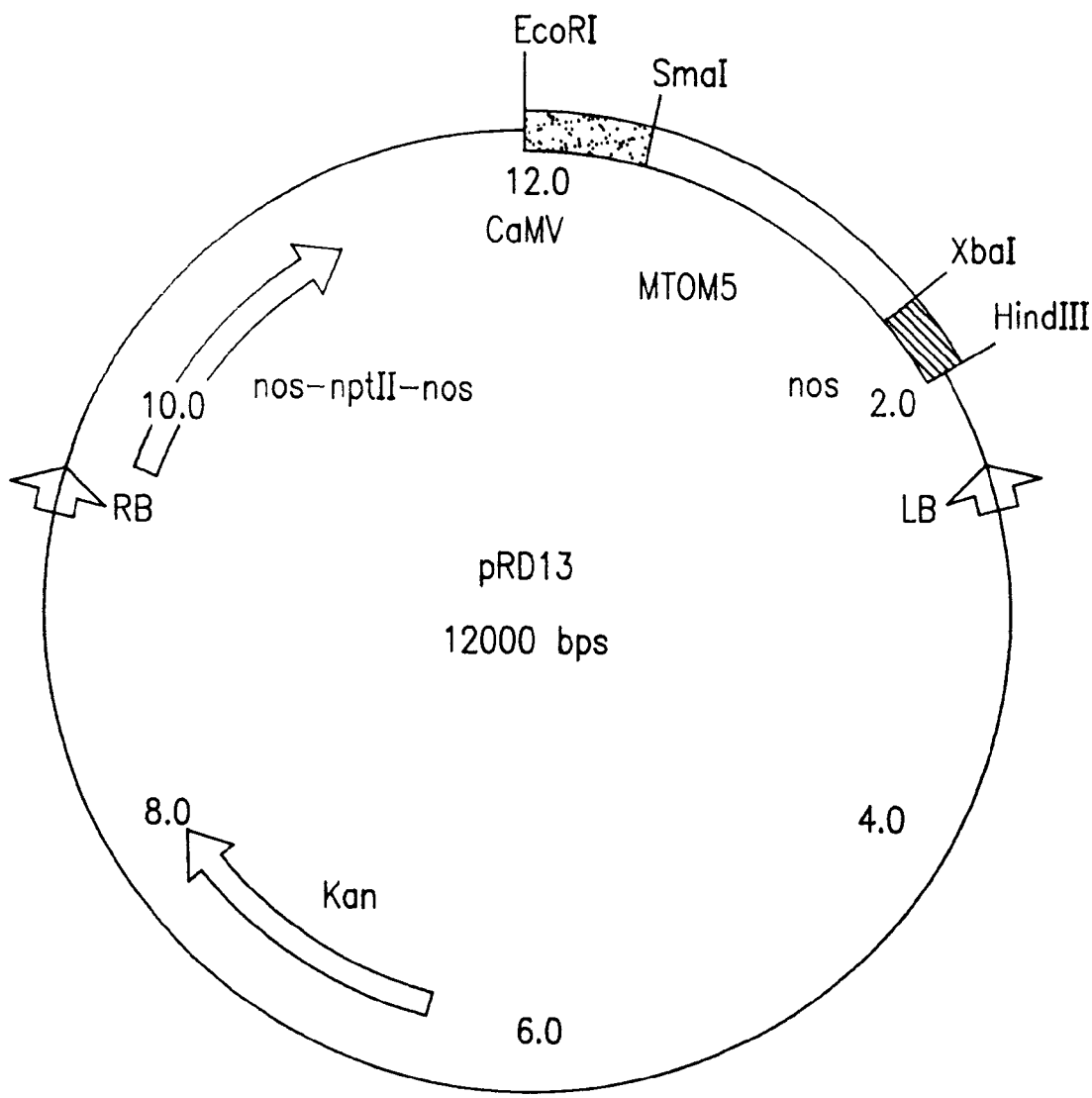
FIG. 2 shows the clone pRD13.

In simple terms, our invention requires that protein expression be enhanced by inserting a gene construct which is altered, with respect to the gene already present in the genome, by maximising the dissimilarity of nucleotide usage while maintaining identity of the encoded protein. In other words, the concept is to express the same protein from genes which have different nucleotide sequences within their coding region and, preferably the promoter region as well. It is desirable to approximate the nucleotide usage (the purine to pyrimidine ratio) of the inserted gene to that of the gene already present in the genome. We also believe it to be desirable to avoid the use of codons in the inserted gene which are uncommon in the target organism and to approximate the overall codon usage to the reported codon usage for the target genome.

The degree to which a sequence may be modified depends on the frequency of degenerate codons. In some instances a high proportion of changes may be made, particularly to the third nucleotide of a triplet, resulting in a low DNA (and consequently RNA) sequence homology between the inserted gene and the gene already present while in other cases, because of the presence of unique codons, the number of changes which are available may be low. The number of changes which are available can be determined readily by a study of the sequence of the gene which is already present in its degeneracy.

To obtain the gene for insertion in accordance with this invention it may be necessary to synthesise it. The general parameters within which the nucleotide sequence of the synthetic gene compared with the gene already present may be selected are:

1. Minimise the nucleotide sequence similarity between the synthetic gene and the gene already present in the plant genome;
2. Maintain the identity of the protein encoded by the coding region;
3. Maintain approximately the optimum codon usage indicated for the target genome;
4. Maintain approximately the same ratio of purine to pyrimidine bases; and
5. Change the promoter or, at least, the 5'-intervening region.

We have worked with the phytoene synthase gene of tomato. The DNA sequence of the endogenous phytoene sequence is known (EMBL Accession Number Y00521): and it was discovered that this gene contained two sequencing errors toward the 3' end. These errors were corrected in the following way (1) cancel the cytosine at location 1365 and (2) insert a cytosine at 1421. The corrected phytoene synthase sequence (Bartley et al 1992), is given herein as SEQ-ID-NO-2. Beginning with that natural sequence we selected modifications according to the parameters quoted above and synthesised the modified gene which we designated MTOM5 and which has the sequence SEQ-ID-NO-1. An alignment of the natural and synthesised gene with retained nucleotides indicated by dots and alterations by dashes is shown here. The modified gene MTOM5 has 63% homology at the DNA level, 100% at the protein level and the proportion of adenine plus thymidine (i.e. the purines) is 54% in the modified gene compared with 58% for the natural sequence.

In the sequence listings provided herewith, SEQ ID NO 1 is the DNA sequence of the synthetic (modified TOM5) gene referred to as MTOM5 in the Sequence Alignment of Modified TOM5 with the synthetic MTOM5 SEQ ID NO 2 is the natural genomic phytoene synthase (PsyI) gene referred to as GTOM5 in the Sequence Alignment, and SEQ-ID NO 3 is the translation product of both GTOM5 and MTOM5.

In tomato (*Lycopersicon esculentum*), it has been shown that the carotenoid namely lycopene, is primarily responsible for the red colouration of developing fruit (Bird et al 1991). The production of an enzyme phytoene synthase, referred to herein as PsyI, is an important catalyst in the production of phytoene, a precursor of lycopene.

PsyI catalyses the conversion of geranyl geranyl diphosphate to phytoene, the first dedicated step in carotenoid biosynthesis.

The regulation and expression of the active PsyI gene is necessary for the production of lycopene and consequently the red colouration of fruit during ripening. This can be illustrated by the yellow flesh phenotype of tomato fruits observed in a naturally occurring mutant in which the PsyI gene is inactive. In addition transgenic plants containing an antisense PsyI transgene, which specifically down regulates PsyI expression have also produced the yellow flesh phenotype of the ripe fruit.

When transgenic plants expressing another copy of the PsyI gene (referred to as TOM5) placed under the control of a constitutive promoter (being the Cauliflower Mosaic Virus 35S promoter) were produced, approximately 30% of the primary transformants produced mature yellow fruit indicative of the phenomenon of co-suppression. Although some of the primary transformants produced an increased caroteniod content, subsequent generations did not exhibit this phenotype thus providing evidence that co-suppression is not always immediate and can occur in future generations.

The sequence of PsyI is known and hence the amino acid sequence was determined.

With reference to published Genbank genetic sequence data (Ken-nosuke Wada et al 1992.), a synthetic DNA was produced by altering the nucleotide sequence to one which still had a reasonable frequency of codon use in tomato, and which retained the amino acid sequence of PsyI. A simple swap between codons was used in cases where there are only two codon options, however in other cases the codons were changed within the codon usage bias of tomato. Nucleotide sequence analysis indicated that the synthetic DNA has a nucleotide similarity with PsyI (TOM5 Bartley et al 1992) of 63% and amino acid sequence similarity of 100%.

The synthetic gene was then cloned into plant transformation vectors under the control of 35S promoter. These were then transferred into tomato plants by Agrobacterium transformation, and both the endogenous and the synthetic gene appear to express the protein. Analysis of the primary transformants illustrates there is no evidence, such as the production of yellow fruit, indicative of co-suppression between the two genes.

The present invention will now be described by way of illustration in the following examples.

EXAMPLE 1

The coding region of the cDNA which encodes tomato phytoene synthase, TOM5 (EMBL accession number Y00521) was modified since the original sequence contained two errors towards the 3' end of the sequence. The sequence reported by Bartley et al 1992 (J Biol Chem 267:5036–5039) for TOM5 cDNA homologues therefore differs from TOM5 (EMBL accession number Y00521). For the purpose of the production of the synthetic gene the sequence used is a corrected version of the TOM5 cDNA which is identical to PsyI (Bartley et al 1992).

Design of the sequence.

1. Potential restriction endonuclease cleavage sites were considered given the constraints of the amino acid sequence. Useful sites around the predicted target sequence cleavage site were introduced to aid subsequent manipulation of the leader.
2. A simple swap between codons was used in cases where there are only two codon options (eg. lysine). In other cases codons were changed within the codon usage bias of tomato as given by Ken-nosuke Wada et al (codon usage tabulated from GenBank genetic sequence data, 1992. Nucleic Acids research 20:S2111–2118). A priority was given to reducing homology and avoiding uncommon codons rather than producing a representative spread of codon usage.
3. A BamHI site was introduced at either end of the sequence to facilitate cloning into the initial. At the 5' end 4A were placed upstream of the ATG according the dicot start site consensus sequence (Cavener and Ray 1991, Eukaryotic start and stop translation sites. NAR 19:3185–3192).
4. The synthetic gene has been cloned into the vector pGEM4Z such that it can be translated using SP6.
5. Restriction site, stemloop and codon usage analyses were performed, all results being satisfactory.
6. The modified TOM5 sequence was termed CGS48 or MTOM5.

Sequence analysis

| | |
|---|---|
| CGS48 | AT content = 54% |
| TOM5 | AT content = 58% |

The nucleotide homology between TOM5 and CGS48 is 63%.

Amino acid sequence homology is 100%.

In summary the sequence TOM5 (Acc. No. Y00521) was extracted from the GenBank database and modified to incorporate the following corrections: deleted C at 1365, inserted C at 1421. CGS48 is based on the CDS of the modified Y00521 and the original sequence, whilst retaining translation product homology and trying to maintain optimal tomato codon usage.

Assembly of CGS48

CGS48 was divided into three parts:

CGS48A: BamHI/KpnI

CGS48B: KpnI/SacI

CGS48C: SacI/BamHI

All three were designed to be cloned on EcoRI/HindIII fragments. The sequences were divided into oligonucleotide fragments following computer analysis to give unique complementarity in the overlapping regions used for the gene assembly.

The oligonucleotides were synthesised on an Applied Biosystems 380B DNA synthesiser using standard cyanoethyl phosphoramidite chemistry. The oligonucleotides were gel purified and assembled into full length fragments using our own procedures.

The assembled fragments were cloned into pUC18 via their EcoRI/HindIII overhangs.

Clones were sequenced bi-directionally using "forward" and "reverse" sequencing primers together with the appropriate "build" primers for the top and bottom strands, using the dideoxy-mediated chain termination method for plasmid DNA.

Inserts from correct CGS48A, B and C clones were isolated by digestion with BamHI/KpnI, KpnI/SacI, SacI/BamHI respectively. The KpnI and SacI ends of the BamHI/KpnI and SacI/BamHI fragments were phosphatased. All three fragments were co-ligated into BamHI cut and phosphatased pGEM4Z. Clones with the correct sized inserts oriented with the 5' end of the insert adjacent to the SmaI site were identified by PCR amplification of isolated colonies and digestion of purified plasmid DNA with a selection of restriction enzymes.

A CsCl purified plasmid DNA preparation was made from one of these clones. This clone (CGS48) was sequenced bi-directionally using "forward" and "reverse" sequencing primers together with the appropriate "build" primers for the top and bottom strands, using the dideoxy-mediated chain termination method for plasmid DNA.

EXAMPLE 2

Construction of the MTOM 5 vector with the CaMV 35S promoter

The fragment MTOM5 (CGS48) DNA described in EXAMPLE 1 was cloned into the vector pJR1Ri (FIG. 1) to give the clone pRD13 (FIG. 3). The clone CGS48 was digested with SmaI and XbaI and then cloned into pJR1Ri which was cut with SmaI and XbaI to produce the clone pRD13.

EXAMPLE 3

Generation and analysis of plants transformed with the vector pRD13

The pDR13 vector was transferred to *Agrobacterium tumefaciens* LBA4404 (a micro-organism widely available to plant biotechnologists) and used to transform tomato plants. Transformation of tomato stem segments followed standard protocols (e.g. Bird et al Plant Molecular Biology 11, 651–662, 1988). Transformed plants were identified by their ability to grow on media containing the antibiotic kanamycin. Forty nine individual plants were regenerated and grown to maturity. None of these plants produced fruit which changed colour to yellow rather than red when ripening. The presence of the pRD13 construct in all of the plants was confirmed by polymerase chain reaction analysis. DNA blot analysis on all plants indicated that the insert copy number was between one and seven. Northern blot analysis on fruit from one plant indicated that the MTOM5 gene was expressed. Six transformed plants were selfed to produce progeny. None of the progeny plants produced fruit which changed colour to yellow rather than red during ripening.

The results are summarised in Table 1 below. The incidence of yellow, or mixed yellow/red (for example, striped) fruits is indicative of suppression of phytoene synthesis. Thus, with the normal GTOM5 construct, 28% of the transgenic plants displayed the co-suppressed phenotype. All the plants carrying the modified MTOM5 construct of this invention had red fruit demonstrating that no suppression of phytoene synthesis had occurred in any of them.

TABLE 1

| | Construct | |
|---|---|---|
| | 35S-GTOM5-nos | 35S-MTOM5-nos |
| Total number of fruiting plants | 39 | 49 |
| Number of plants producing yellow fruit | 8 | 0 |
| Number of plants producing mixed yellow and red fruit or temporal changes | 3 | 0 |
| Number of plants producing red fruit | 28 | 49 |
| % plants showing co-suppression of psyI | 28% | 0% |

```
TOM5   ATG TCT GTT GCC TTG TTA TGG GTT GTT TCT  30
       ... --- ..- ..- -.- -.- ... ..- ..- ---
MTOM5  ATG AGC GTG GCA CTT CTT TGG GTG GTG AGC  30
       M   S   V   A   L   L   W   V   V   S

TOM5   CCT TGT GAC GTC TCA AAT GGG ACA AGT TTC  60
       ..- ..- ..- ..- --- ..- ..- --- --- ..-
MTOM5  CCA TGC GAT GTG AGT AAC GGC ACT TCA TTT  60
       P   C   D   V   S   N   G   T   S   F

TOM5   ATG GAA TCA GTC CGG GAG GGA AAC CGT TTT  90
       ... ..- --- ..- -.- ... ... ..- -.- ..-
MTOM5  ATG GAG AGT GTG AGA GAA GGT AAT AGA TTC  90
       M   E   S   V   R   E   G   N   R   F

TOM5   TTT GAT TCA TCG AGG CAT AGG AAT TTG GTG  120
       ..- ..- --- ..- -.- ... -.- ..- -.- ..-
MTOM5  TTC GAC AGT TCT CGT CAC CGT AAC CTT GTT  120
       F   D   S   S   R   H   R   N   L   V

TOM5   TCC AAT GAG AGA ATC AAT AGA GGT GGT GGA  150
       --- ..- ..- -.- ..- ..- ..- ..- ..- ..-
MTOM5  AGT AAC GAA CGT ATA AAC AGG GGA GGA GGT  150
       S   N   E   R   I   N   R   G   G   G

TOM5   AAG CAA ACT AAT AAT GGA CGG AAA TTT TCT  180
       ..- ..- ..- ..- ..- ... -.- ..- ..- ..-
MTOM5  AAA CAG ACA AAC AAC GGT AGA AAG TTC TCA  180
       K   Q   T   N   N   G   R   K   F   S
```

-continued

```
TOM5   GTA CGG TCT GCT ATT TTG GCT ACT CCA TCT 210
       ..- -.- ..- ..- ..- -.- ..- ..- ..- ---
MTOM5  GTT AGA TCA GCA ATC CTT GCA ACA CCT AGC 210
       V   R   S   A   I   L   A   T   P   S

TOM5   GGA GAA CGG ACG ATG ACA TCG GAA CAG ATG 240
       ..- ..- -.- ..- ..- ..- ..- ..- ..- ...
MTOM5  GGT GAG AGA ACT ATG ACT AGC GAG CAA ATG 240
       G   E   R   T   M   T   S   E   Q   M

TOM5   GTC TAT GAT GTG GTT TTG AGG CAG GCA GCC 270
       ..- ..- ..- ..- ..- ..- ..- ..- ..- ..-
MTOM5  GTG TAC GAC GTC GTA CTT CGT CAA GCT GCA 270
       V   Y   D   V   V   L   R   Q   A   A

TOM5   TTG GTG AAG AGG CAA CTG AGA TCT ACC AAT 300
       -.- ..- -.- ..- -.- ..- --- ..- ..- ...
MTOM5  CTA GTT AAA CGT CAG TTA CGT AGT ACT AAC 300
       L   V   K   R   Q   L   R   S   T   N

TOM5   GAG TTA GAA GTG AAG CCG GAT ATA CCT ATT 330
       ..- ..- -.- ..- ..- ..- ..- ..- ..- ...
MTOM5  GAA CTT GAG GTT AAA CCT GAC ATT CCA ATA 330
       E   L   E   V   K   P   D   I   P   I

TOM5   CCG GGG AAT TTG GGC TTG TTG AGT GAA GCA 360
       ..- ..- ..- -.- ..- -.- -.- --- ..- ..-
MTOM5  CCT GGA AAC CTT GGA CTT CTT TCT GAG GCT 360
       P   G   N   L   G   L   L   S   E   A

TOM5   TAT GAT AGG TGT GGT GAA GTA TGT GCA GAG 390
       ..- ..- ..- ..- ..- ..- ..- ..- ..- ..-
MTOM5  TAC GAC AGA TGC GGA GAG GTT TGC GCA GAA 390
       Y   D   R   C   G   E   V   C   A   E

TOM5   TAT GCA AAG ACG TTT AAC TTA GGA ACT ATG 420
       ..- ..- ..- -.- ..- ..- ..- ..- ..- ...
MTOM5  TAC GCT AAA ACC TTC AAT TTG GGT ACC ATG 420
       Y   A   K   T   F   N   L   G   T   M

TOM5   CTA ATG ACT CCC GAG AGA AGA AGG GCT ATC 450
       -.- ... ..- ..- ..- ..- ..- -.- ..- ..-
MTOM5  TTG ATG ACA CCA GAA AGG CGT CGT GCA ATA 450
       L   M   T   P   E   R   R   R   A   I

TOM5   TGG GCA ATA TAT GTA TGG TGC AGA AGA ACA 480
       ... ..- ..- ... ..- ..- ..- -.- ..- ...
MTOM5  TGG GCT ATT TAC GTT TGG TGT AGG CGT ACT 480
       W   A   I   Y   V   W   C   R   R   T

TOM5   GAT GAA CTT GTT GAT GGC CCA AAC GCA TCA 510
       ..- ..- -.- ..- ..- ..- ..- ..- ..- ---
MTOM5  GAC GAG TTA GTG GAC GGA CCT AAT GCT AGT 510
       D   E   L   V   D   G   P   N   A   S

TOM5   TAT ATT ACC CCG GCA GCC TTA GAT AGG TGG 540
       ..- ..- ..- -.- ..- -.- ..- -.- ..- ...
MTOM5  TAC ATA ACC CCC GCT GCT CTT GAC AGA TGG 540
       Y   I   T   P   A   A   L   D   R   W

TOM5   GAA AAT AGG CTA GAA GAT GTT TTC AAT GGG 570
       ..- ..- ..- -.- ..- ..- ..- ..- ..- ..-
MTOM5  GAG AAC CGT TTG GAG GAC GTG TTT AAC GGC 570
       E   N   R   L   E   D   V   F   N   G

TOM5   CGG CCA TTT GAC ATG CTC GAT GGT GCT TTG 600
       -.- ..- ..- ..- ..- ..- ..- ..- ..- -.-
MTOM5  AGA CCT TTC GAT ATG TTG GAC GGA GCA CTT 600
       R   P   F   D   M   L   D   G   A   L

TOM5   TCC GAT ACA GTT TCT AAC TTT CCA GTT GAT 630
       --- ..- ..- --- ..- ..- --- ..- ..- ...
MTOM5  AGT GAC ACT GTG AGC AAT TTC CCT GTG GAC 630
       S   D   T   V   S   N   F   P   V   D

TOM5   ATT CAG CCA TTC AGA GAT ATG ATT GAA GGA 660
       ..- ..- ..- ..- ..- ..- ..- ..- ..- ..-
MTOM5  ATC CAA CCT TTT CGG GAC ATG ATC GAG GGC 660
       I   Q   P   F   R   D   M   I   E   G

TOM5   ATG CGT ATG GAC TTG AGA AAA TCG AGA TAC 690
       ... -.- ... ..- ..- -.- ..- ..- ..- ---
MTOM5  ATG AGA ATG GAT CTT CGT AAG TCT CGT TAT 690
       M   R   M   D   L   R   K   S   R   Y

TOM5   AAA AAC TTC GAC GAA CTA TAC CTT TAT TGT 720
       ..- ..- ..- ..- ..- -.- ..- ..- ..- ..-
MTOM5  AAG AAT TTT GAT GAG TTG TAT TTG TAC TGC 720
       K   N   F   D   E   L   Y   L   Y   C

TOM5   TAT TAT GTT GCT GGT ACG GTT GGG TTG ATG 750
       ..- ..- ..- ..- ..- ..- ..- ..- -.- ...
MTOM5  TAC TAC GTG GCA GGA ACC GTG GGC CTT ATG 750
       Y   Y   V   A   G   T   V   G   L   M

TOM5   AGT GTT CCA ATT ATG GGT ATC GCC CCT GAA 780
       --- ... ..- ... ..- ..- ... ..- ..- ..-
MTOM5  TCA GTG CCT ATC ATG GGA ATT GCA CCA GAG 780
       S   V   P   I   M   G   I   A   P   E

TOM5   TCA AAG GCA ACA ACA GAG AGC GTA TAT AAT 810
       --- ..- ..- ..- ..- ..- --- ..- ..- ..-
MTOM5  AGT AAA GCT ACT ACT GAA TCT GTT TAC ACC 810
       S   K   A   T   T   E   S   V   Y   N

TOM5   GCT GCT TTG GCT CTG GGG ATC GCA AAT CAA 840
       ..- ..- -.- ..- ..- ..- ..- ..- ..- ..-
MTOM5  GCA GCA CTA GCA CTT GGT ATA GCT AAC CAG 840
       A   A   L   A   L   G   I   A   N   Q

TOM5   TTA ACT AAC ATA CTC AGA GAT GTT GGA GAA 870
       -.- ..- ..- ..- ..- -.- ..- ..- ..- ..-
MTOM5  CTT ACA AAT ATC TTG AGG GAC GTG GGT GAG 870
       L   T   N   I   L   R   D   V   G   E

TOM5   GAT GCC AGA AGA GGA AGA GTC TAC TTG CCT 900
       ..- ..- -.- ..- ..- -.- ..- ..- -.- ..-
MTOM5  GAC GCA CGT AGG GGT CGT GTG TAT CTC CCA 900
       D   A   R   R   G   R   V   Y   L   P

TOM5   CAA GAT GAA TTA GCA CAG GCA GGT CTA TCC 930
       ..- ..- ..- -.- ..- ..- ..- ..- -.- ---
MTOM5  CAG GAC GAG CTC GCT CAA GCT GGA TTG AGT 930
       Q   D   E   L   A   Q   A   G   L   S

TOM5   GAT GAA GAT ATA TTT GCT GGA AGG GTG ACC 960
       ..- ... ..- ..- ..- ..- ..- ..- ..- ..-
MTOM5  GAC GAG GAC ATT TTC GCA GGT CGT GTT ACA 960
       D   E   D   I   F   A   G   R   V   T

TOM5   GAT AAA TGG AGA ATC TTT ATG AAG AAA CAA 990
       ..- ..- ..- ..- ..- ..- ... ..- ..- ..-
MTOM5  GAC AAG TGG AGG ATT TTC ATG AAA AAG CAG 990
       D   K   W   R   I   F   M   K   K   Q

TOM5   ATA CAT AGG GCA AGA AAG TTC TTT GAT GAG 1020
       ..- ... ..- -.- ..- -.- ..- ..- ..- ..-
MTOM5  ATT CAC CGT GCT GCT CGT AAA TTT TTC GAC GAA 1020
       I   H   R   A   R   K   F   F   D   E

TOM5   GCA GAG AAA GGC GTG ACA GAA TTG AGC TCA 1050
       ..- ..- ..- ..- ..- ..- ..- --- ..- ---
MTOM5  GCT GAA AAG GGA GTT ACT GAG CTT TCT AGT 1050
       A   E   K   G   V   T   E   L   S   S

TOM5   GCT AGT AGA TTC CCT GTA TGG GCA TCT TTG 1080
       ..- --- ..- ..- ..- ..- ..- --- ..- -.-
MTOM5  GCA TCA AGG TTT CCA GTT TGG GCC AGC TTT 1080
       A   S   R   F   P   V   W   A   S   L

TOM5   GTC TTG TAC CGC AAA ATA CTA GAT GAG ATT 1110
       ..- -.- ..- ..- ..- ..- ..- ..- ..- ..-
MTOM5  GTG CTC TAT AGA AAG ATT TTG GAC GAA ATC 1110
       V   L   Y   R   K   I   L   D   E   I

TOM5   GAA GCC AAT GAC TAC AAC AAC TTC ACA AAG 1140
       ..- ..- ..- ..- ..- ..- ..- ..- ..- ..-
MTOM5  GAG GCT AAC GAT TAT AAT AAT TTT ACT AAA 1140
       E   A   N   D   Y   N   N   F   T   K
```

-continued

```
TOM5  AGA GCA TAT GTG AGC AAA TCA AAG AAG TTG  1170
      -.- ..- ..- ... --- ..- --- ... ..- -.-
MTOM5 CGT GCT TAC GTT TCT AAG AGC AAA AAA CTT  1170
       R   A   Y   V   S   K   S   K   K   L

TOM5  ATT GCA TTA CCT ATT GCA TAT GCA AAA TCT  1200
      ..- ..- -.- ... ..- ... ..- ... ..- ---
MTOM5 ATC GCT CTT CCA ATC GCT TAC GCT AAG AGC  1200
       I   A   L   P   I   A   Y   A   K   S

TOM5  CTT GTG CCT CCT ACA AAA ACT GCC TCT CTT  1230
      -.- ..- ... ... ..- ... ... ... --- -.-
MTOM5 TTG GTT CCA CCA ACT AAG ACA GCT AGC TTG  1230
       L   V   P   P   T   K   T   A   S   L

TOM5  CAA AGA TAA                              1239
      ..- ..- .-.
MTOM5 CAG AGG TGA                              1239
       Q   R   *
```

. = Same Base
- = Different Base

SEQUENCE: 63% HOMOLOGY
PROTEIN SEQUENCE: 100% HOMOLOGY

---

What is claimed is:

1. A method of enhancing the level of phytoene synthase in a plant having an endogenous gene which produces phytoene synthase comprising inserting into the genome of said plant the DNA sequence of SEQ ID NO: 1.

2. The method as claimed in claim 1 wherein said plant is a tomato plant.

3. A gene construct comprising in sequence a promoter which is operable in a plant, the DNA sequence of SEQ ID NO: 1 and a termination signal.

4. A method of enhancing the level of carotenoid production in a plant having an endogenous phytoene synthase gene comprising expressing in said plant the DNA of SEQ ID NO: 1.

5. The method as claimed in claim 4 wherein said plant is a tomato plant.

* * * * *